US006660172B2

(12) United States Patent
Koslow

(10) Patent No.: US 6,660,172 B2
(45) Date of Patent: Dec. 9, 2003

(54) PRECOAT FILTRATION MEDIA AND METHODS OF MAKING AND USING

(75) Inventor: Evan E. Koslow, Weston, CT (US)

(73) Assignee: Koslow Technologies Corporation, Orange, CT (US)

( * ) Notice: Subject to any disclaimer, the term of this patent is extended or adjusted under 35 U.S.C. 154(b) by 0 days.

(21) Appl. No.: 10/300,955

(22) Filed: Nov. 20, 2002

(65) Prior Publication Data

US 2003/0141261 A1 Jul. 31, 2003

Related U.S. Application Data

(63) Continuation-in-part of application No. 10/286,695, filed on Nov. 1, 2002.
(60) Provisional application No. 60/354,062, filed on Jan. 31, 2001.

(51) Int. Cl.[7] .............................. C02F 1/00; B01D 39/00
(52) U.S. Cl. ...................... 210/777; 210/508; 210/767; 210/663; 210/502.1; 502/62; 502/63; 502/65; 502/82
(58) Field of Search ................................. 210/777, 508, 210/767, 663, 502.1; 502/62, 63, 65, 82; 424/78.17, 78.09

(56) References Cited

U.S. PATENT DOCUMENTS

| | | | |
|---|---|---|---|
| 3,958,023 A | | 5/1976 | Butterworth |
| 4,238,334 A | * | 12/1980 | Halbfoster |
| 4,313,832 A | * | 2/1982 | Shimizu et al. |
| 4,572,742 A | * | 2/1986 | Kunin et al. |
| 4,734,208 A | * | 3/1988 | Pall et al. |
| 4,927,796 A | * | 5/1990 | D'Angelo et al. |
| 4,973,404 A | | 11/1990 | Weber et al. |
| 5,055,314 A | | 10/1991 | Fernyhough |
| 5,114,894 A | | 5/1992 | Witt |
| 5,385,678 A | | 1/1995 | Witt |
| 5,439,699 A | | 8/1995 | Tripp et al. |
| 5,589,076 A | | 12/1996 | Womack |
| 5,681,465 A | | 10/1997 | Takenoya et al. |
| 6,126,931 A | * | 10/2000 | Sawan et al. |
| 6,332,977 B1 | | 12/2001 | Janecek |
| 6,471,876 B1 | * | 10/2002 | Hansen et al. |

FOREIGN PATENT DOCUMENTS

| | | |
|---|---|---|
| EP | 0337354 A1 | 10/1989 |
| WO | WO 02/36730 | 5/2002 |

* cited by examiner

Primary Examiner—Ana M. Fortuna
(74) Attorney, Agent, or Firm—Shirley S. Ma

(57) ABSTRACT

The invention is directed to a precoat or body feed composition comprising a microbiological interception enhanced filter aid. Preferably, the microbiological interception enhanced filter aid comprises fibrillated lyocell nanofibers having coated on at least a portion of a surface thereof, a microbiological interception enhancing agent. The microbiological interception enhanced agent comprises a cationic material in combination with a biologically active metal. At least about 4 log reduction in bacterial interception is achieved with the microbiological interception enhanced filter aid alone or in combination with a bulk, untreated filter aid. A precoat composition including the microbiological interception enhanced filter aid can be used for one-step cold sterilization of beverages.

20 Claims, No Drawings

PRECOAT FILTRATION MEDIA AND METHODS OF MAKING AND USING

This application is a continuation-in-part U.S. application Ser. No. 10/286,695 filed on Nov. 1, 2002, and from U.S. Provisional Application Serial No. 60/354,062 filed on Jan. 31, 2001.

The present invention is directed to a filter aid useful in precoat filtration systems for separating solids from liquids, in particular, beverages.

Mechanical methods of filtration typically operate by physical exclusion. A contaminated influent is passed through a porous medium that retains particles larger in size than the size of the pores of the porous medium and permits passage of an effluent that contains particles smaller in size than the size of the pores of the porous medium. There is a balance between capturing the smallest possible particles in the contaminated influent with the flow rate of the influent passing through the porous medium that must be achieved to provide high throughput.

It is known in the prior art to filter beverages, particularly fermented beverages, using a porous bed or powder filtration system. For example, beer or wine is filtered after fermentation to remove yeast and other turbidity causing materials in order to achieve colloidal and microbiological stability. During powder filtration, a precoat of filter aid, generally a porous material such as diatomaceous earth or cellulose fibers having a specific pore size is formed on a septum. As a dispersion of the filter aid is passed through the septum, the filter aid fibers or particles that are too large to pass through the pores of the septum build up on the septum forming a filter cake. Filter aid fiber or particles smaller than the pores of the septum will eventually be lodged behind the larger filter aid fibers or particles providing a distribution of pore sizes in the filter cake for optimum filtration.

In order to provide a deep polishing of the fluid, a single filtration pass is insufficient, therefore, multiple filtration steps are necessary. In order to remove microbiological contaminants, such as yeast used in making fermented beverages, the pore size of the filter must be on the order of less than about 10 microns. Furthermore, cold sterilization techniques require a pore size of less than about 2 microns. Prior art filtration systems using a precoat have been unsuccessful in providing a deep polishing of the fluid without the use of multiple filtration steps or providing a single-step cold sterilization of the fluid.

SUMMARY OF THE INVENTION

In a first aspect, the present invention is directed to a composition comprising: a filter aid having coated on at least a portion thereof, a cationic material having a counter ion associated therewith, wherein a biologically active metal is precipitated with the counter ion in direct proximity to the cationic material.

In another aspect, the present invention is directed to a composition comprising: an adsorbent; a filter aid admixed with the adsorbent, the filter aid having coated on at least a portion thereof, a cationic material having a counter ion associated therewith and a biologically active metal precipitated with the counter ion in direct proximity to the cationic material.

In yet another aspect, the present invention is directed to a method of filtering an influent: providing a support medium; coating the support medium with a filter aid to form a precoat, the filter aid having coated on at least a portion thereof, a cationic material having a counter ion associated therewith and a biologically active metal precipitated with the counter ion in direct proximity to the cationic material; passing the influent through the precoat; retaining contaminants from the influent on the precoat; and obtaining a clarified effluent.

DETAILED DESCRIPTION OF THE PREFERRED EMBODIMENT(s) DEFINITIONS

The following terms in either singular or plural form shall have the following meanings throughout the specification.

"Absorbent" shall mean any material that is capable of absorbing impurities primarily by drawing the impurities into its inner structure.

"Adsorbent" shall mean any material that is capable of adsorbing impurities primarily by physical adsorption to its surface.

"Bulk filter aid" shall mean those materials traditionally used as precoat materials and/or body feed compositions that are not charge modified. These materials include, but are not limited to, activated carbon, perlite, diatomaceous earth, cellulose, silica, and the like.

"Contaminant reductions" shall mean attenuation of an impurity in a fluid that is intercepted, removed, or rendered inactive, chemically, mechanically or biologically, in order to render the fluid safer as, for example for human use, or more useful, as in industrial applications.

"Fiber" shall mean a solid that is characterized by a high aspect ratio of length to diameter of, for example, several hundred to one. Any discussion of fibers includes whiskers.

"Filter aid" or "filter aid material" shall mean a material useful in precoat filtration systems for removing contaminants from a fluid.

"Filter medium" shall mean a material that performs fluid filtration.

"Fluid" shall mean a liquid, gas, or combination thereof.

"Intercept" or "interception" are taken to mean interfering with, or stopping the passage of, so as to affect, remove, inactivate or influence.

"Log reduction value" or "LRV" shall mean the log$_{10}$ of the number of organisms in the influent divided by the number of organisms in the effluent of a filter.

"Microbiological interception enhanced filter aid" shall mean a filter aid or a portion thereof that includes a cationically charged filter aid having coated on at least a portion thereof, a cationic material in combination with a biologically active metal. Additional additives can be added to make the microbiological interception enhanced filter aid more useful for its intended purpose.

"Microbiological interception enhancing agent" shall mean a cationic material having a counter ion associated therewith in combination with a biologically active metal.

"Microorganism" shall mean any living organism that can be suspended in a fluid, including but not limited to bacteria, viruses, fungi, protozoa, and reproductive forms thereof including cysts and spores.

"Particle" shall mean a solid having a size range from the colloidal to macroscopic, and with no specific limitation on shape, but generally of a limited length to width ratio.

"Whisker" shall mean a filament having a limited aspect ratio and intermediate between the aspect ratio of a particle and a fiber. Any discussion of fibers includes whiskers.

General Precoat Composition Characteristics

The precoat composition of the present invention includes a microbiological interception enhanced filter aid that provides enhanced filtration including microbiological interception capability using a combination of an appropriate pore structure and a chemical treatment. The microbiological interception enhanced filter aid when used as the sole ingredient of a precoat composition provides a pore size of less than about 2 microns, and can be less than about 1 micron. When used in combination with a bulk filter aid, the microbiological interception enhanced filter aid enhances filter performance, extends filter life, and provides a more robust filter cake. When the microbiological interception enhanced filter aid is mixed with a bulk filter aid, the pore size and charge on at least a portion of the material allows interception of smaller contaminants. Specific filtration needs can be met by combining the microbiological interception enhanced filter aid with the bulk filter aid in varying amounts. The microbiological interception enhanced filter aid material may also be used as a body feed composition.

The microbiological interception enhanced filter aid comprises any material that is capable of having a mean flow path of less than about 2.0 microns. Preferably, the microbiological interception enhanced filter aid comprises nanofibers and/or whiskers, or active particles, alone or in combination, treated with a microbiological interception enhancing agent. The tight pore structure of a resultant filter cake provided by the precoat composition of the present invention provides short diffusion distances from the fluid to the surface of the filter cake. The chemical treatment process used to treat the surface of the microbiological interception enhanced filter aid utilizes a synergistic interaction between a cationic material and a biologically active metal, that when combined, provide broad-spectrum reduction of microbiological contaminants on contact. The charge provided by the cationic material to the microbiological interception enhanced filter aid provides enhanced electro-kinetic interception of microbiological contaminants, while the tight pore structure provides a short diffusion path and, therefore, rapid diffusion kinetics of contaminants in a flowing fluid to the surface of the precoat composition. The microbiological interception enhanced filter aid also provides supplemental direct mechanical interception of microbiological contaminants.

The microbiological interception enhanced filter aid may comprise of any material capable of retaining a charge, as determined by streaming or zeta potential, on at least a portion of its surface. When the precoat composition is used to filter beverages, a food-safe, hydrophilic material that is insoluble in water is preferred. The microbiological interception enhanced filter aid can be organic or inorganic fibers, whiskers, powders, and/or particulates. Preferably, the microbiological interception enhanced filter aid can be comprised of activated carbon, perlite, diatomaceous earth, cellulose, silica, and the like. The chemical treatment process used to treat the surface of the microbiological interception enhanced filter aid utilizes a synergistic interaction between a cationic material and a biologically active metal, that when combined, provide at least about 3 log reduction of bacterial contaminants. The charge provided by the cationic material to the microbiological interception enhanced filter aid supports electro-kinetic interception of bacterial contaminants and other negatively charged particulates undesirable in the effluent.

The Filter Aid Material

The precoat composition of the present invention comprises a microbiological interception enhanced filter aid having coated on at least a portion thereof, a cationic material having a counter ion associated therewith and a biologically active metal precipitated with the counter ion in direct proximity to the cationic material. Preferably, the microbiological interception enhanced filter aid is comprised of a plurality of nanofibers and/or particulate ingredients of organic and inorganic materials including, but not limited to, polymers, ion-exchange resins, engineered resins, ceramics, cellulose, asbestos, glass, metal, activated alumina, carbon or activated carbon, silica, zeolites, diatomaceous earth, perlite, activated bauxite, fuller's earth, calcium hydroxyappatite, other adsorbent materials, or combinations thereof. Combinations of organic and inorganic fibers and/or whiskers or particles are contemplated and within the scope of the invention as for example, glass, ceramic, metal fibers and polymeric fibers can be used together with very small particulate adsorbents or particles that can be formulated into a precoat composition.

The precoat composition can be comprised entirely of the microbiological interception enhanced filter aid or can contain only a portion thereof. One preferred embodiment of the precoat composition comprises filter aid material of substantially nanofibers treated in accordance with the present invention. Preferably, the nanofibers are cellulose or polymer fibers that have a Canadian Standard Freeness of less than or equal to about 100, and most preferably less than or equal to about 45. Preferably, a significant portion of the fibers should have a diameter less than or equal to about 1000 nanometers, more preferably less than or equal to about 400 nanometers, and fibers less than or equal to about 250 nanometers in diameter are most preferred. It is preferable to chop the fibers to a length of about 1 millimeter to about 8 millimeters, preferably about 2 millimeters to about 6 millimeters, and more preferably about 3 millimeters to about 4 millimeters. Fibrillated fibers are most preferred due to their exceptionally fine dimensions and potentially low cost.

Preferably, fibrillated synthetic cellulose fibers, processed in accordance with the present invention, can produce an ultra-fine, hydrophilic microbiological interception enhanced filter aid for use in a precoat composition of the present invention. Such fibrillated cellulose fibers can be made by direct dissolution and spinning of wood pulp in an organic solvent, such as an amine oxide, and are known as lyocell fibers. Lyocell fibers have the advantage of being produced in a consistent, uniform manner, thus yielding reproducible results, which may not be the case with, for example, natural cellulose fibers. Further, the fibrils of lyocell are often curled. The curls provide a significant amount of fiber entanglement, resulting in a significant residual wet strength. Furthermore, the fibrillated lyocell fibers may be produced in large quantities using equipment of modest capital cost. It will be understood that fibers other than cellulose may be fibrillated to produce extremely fine fibrils, such as for example, synthetic fibers, in particular, acrylic or nylon fibers, or other natural cellulosic materials. Combinations of fibrillated and non-fibrillated fibers may be used in making the microbiological interception enhanced filter aid.

The Microbiological Interception Enhancing Agent

The filter aid material is chemically treated with a microbiological interception enhancing agent capable of creating a positive charge on the surface of the filter aid material. The chemical treatment produces a strong positive charge upon the treated surfaces as measured using streaming or zeta potential analysis and this positive charge is retained at pH values below 10. The cationic material may be a small charged molecule or a linear or branched polymer having positively charged atoms along the length of the polymer chain having a counter ion associated therewith. The cationic material is adsorbed on at least a portion of the filter aid material and a biologically active metal is precipitated with the counter ion in direct proximity to the cationic material and also on at least a portion of the filter aid material.

If the cationic material is a polymer, the charge density is preferably greater than about 1 charged atom per about every 30 Angstroms, preferably greater than about 1 charged atom per about every 20 Angstroms, and more preferably greater than about 1 charged atom per about every 10 Angstroms of molecular length. The higher the charge density on the cationic material, the higher the concentration of the counter ion associated therewith. A high concentration of an appropriate counter ion can be used to drive the precipitation of the biologically active metal. The high charge density of the cationic material provides the ability to adsorb and significantly reverse the normal negative charge of the raw materials useful in making the microbiological interception enhanced filter aid. The cationic material should consistently provide a highly positively charged surface to the microbiological interception enhanced filter aid as determined by a streaming or zeta potential analyzer, whether in a high or low pH environment.

The use of a cationic polymer of sufficiently high molecular weight allows treatment of the surfaces of the microbiological interception enhanced filter aid without serious attendant impact upon any adsorptive capabilities of the mezo-pores and micro-pores of filter aid materials such as activated carbon. The cationic material can have a molecular weight greater than or equal to about 5000 Daltons, preferably greater than or equal to 100,000 Dalton, more preferably greater than or equal to about 400,000 Daltons, and can be greater than or equal to about 5,000,000 Daltons.

The cationic material includes, but is not limited to, quaternized amines, quaternized amides, quaternary ammonium salts, quaternized imides, benzalkonium compounds, biguanides, cationic aminosilicon compounds, cationic cellulose derivatives, cationic starches, quaternized polyglycol amine condensates, quaternized collagen polypeptides, cationic chitin derivatives, cationic guar gum, colloids such as cationic melamine-formaldehyde acid colloids, inorganic treated silica colloids, polyamide-epichlorohydrin resin, cationic acrylamides, polymers and copolymers thereof, combinations thereof, and the like. Charged molecules useful for this application can be small molecules with a single charged unit and capable of being attached to at least a portion of the filter aid material. The cationic material preferably has one or more counter ions associated therewith which, when exposed to a biologically active metal salt solution, cause preferential precipitation of the metal in proximity to the cationic surface to form a colloidal metal precipitate complex.

Exemplary of amines may be pyrroles, epichlorohydrin derived amines, polymers thereof, and the like. Exemplary of amides may be those polyamides disclosed in International Patent Application No. WO 01/07090, and the like. Exemplary of quaternary ammonium salts may be homopolymers of diallyl dimethyl ammonium halide, epichlorohydrin derived polyquaternary amine polymers, quaternary ammonium salts derived from diamines and dihalides such as those disclosed in U.S. Pat. Nos. 2,261,002, 2,271,378, 2,388,614, and 2,454,547, all of which are incorporated by reference, and in International Patent Application No. WO 97/23594, also incorporated by reference, polyhexamethylenedimethylammonium bromide, and the like. The cationic material may be chemically bonded, adsorbed, or crosslinked to itself and/or to the filter aid material.

Furthermore, other materials suitable for use as the cationic material include BIOSHIELD® available from BioShield Technologies, Inc., Norcross, Georgia. BIOSHIELD® is an organosilane product including approximately 5% by weight octadecylaminodimethyltrimethoxysilylpropyl ammonium chloride and less than 3% chloropropyltrimethoxysilane. Another material that may be used is SURFACINE®, available from Surfacine Development Company LLC, Tyngsboro, Mass. SURFACINE® comprises a three-dimensional polymeric network obtained by reacting poly(hexamethylenebiguanide) (PHMB) with 4,4'-methlyene-bis-N,N-dilycidylaniline (MBGDA), a crosslinking agent, to covalently bond the PHMB to a polymeric surface. Silver, in the form of silver iodide, is introduced into the network, and is trapped as submicron-sized particles. The combination is an effective biocide, which may be used in the present invention. Depending upon the filter aid material, the MBGDA may or may not crosslink the PHMB to the microbiological interception enhanced filter aid.

The cationic material is exposed to a biologically active metal salt solution such that a metal colloidal complex precipitates onto at least a portion of the surface of at least some of the filter aid material. For this purpose, the metals that are biologically active are preferred. Such biologically active metals include, but are not limited to, silver, copper, zinc, cadmium, mercury, antimony, gold, aluminum, platinum, palladium, and combinations thereof. The most preferred biologically active metals are silver and copper. The biologically active metal salt solution is preferably selected such that the metal and the counter ion of the cationic material are substantially insoluble in an aqueous environment to drive precipitation of the metal complex. Preferably, the metal is present in an amount of about 0.01% to about 2.0% by weight of the microbiological interception enhanced filter aid.

A particularly useful microbiological interception enhancing agent is a silver-amine-halide complex. The cationic amine is preferably a homopolymer of diallyl dimethyl ammonium halide having a molecular weight of about 400,000 Daltons or other quaternary ammonium salts having a similar charge density and molecular weight. A homopolymer of diallyl dimethyl ammonium chloride useful in the present invention is commercially available from Nalco Chemical Company of Naperville, Ill., under the tradename MERQUAT 100. The chloride counter ion may be replaced with a bromide or iodide counter ion. When contacted with a silver nitrate solution, the silver-amine-halide complex precipitates on at least a portion of the microbiological interception enhanced filter aid.

Activated carbon is commonly used as a filter aid material for making colorless malt beverages. Where the microbiological interception enhanced filter aid includes activated carbon, the cationic material preferably has a high charge density and a sufficiently high molecular weight to create a strong attraction and high coordination energy with the negatively charged surface groups of activated carbon. Also, the enhanced interception using the charged surface of the activated carbon, in the presence of a colloid of a biologically active metal, is supplemented by the hydrophobic adsorption mechanism of the activated carbon. Untreated portions of the carbon surface, with their oxygen-rich chemistry, tend to have a negative charge that can continue to adsorb positively charged particles. The combination of positive, negative, and hydrophobic surfaces presents a nearly insurmountable barrier for contaminants to navigate.

After treating the filter aid material with the microbiological interception enhancing agent, the presence of the biologically active metal and its associated counter ion on the active particles can be detected using X-ray fluorescence.

Methods of Making the Microbiological Interception Enhanced Filter Aid

The filter aid materials useful in making the microbiological interception enhanced filter aid of the present invention can be treated with the microbiological interception enhancing agent according to processes known to one of skill in the art including spray coating, submergence coating, and the like. An exemplary process is outlined below for making a microbiological interception enhanced filter aid comprising nanofibers treated with the microbiological interception enhancing agent. Similar treatment processes for particulate filter aid material are known to one of skill in the art.

In making a microbiological interception enhanced filter aid comprising nanofibers, a fiber tow is chopped to a specific length, usually in the range of about 1 millimeter to about 8 millimeters, and in particular in the range of about 3 millimeters to about 4 millimeters. The chopped fibers are fibrillated in a device having characteristics similar to a blender, or on a large scale, in machines commonly referred to as a "hi-low", a "beater" or a "refiner". The fiber is subjected to repetitive stresses, while further chopping and the reduction of fiber length is minimized. As the fibers undergo these stresses, the fibers split as a result of weaknesses between amorphous and crystalline regions and the Canadian Standard Freeness (CSF), which is determined by a method well known in the art, begins to decline. Samples of the resulting pulp can be removed at intervals, and the CSF used as an indirect measure of the extent of fibrillation. While the CSF value is slightly responsive to fiber length, it is strongly responsive to the degree of fiber fibrillation. Thus, the CSF, which is a measure of how easily water may be removed from the pulp, is a suitable means of monitoring the degree of fiber fibrillation. If the surface area is very high, then very little water will be drained from the pulp in a given amount of time and the CSF value will become progressively lower as the fibers fibrillate more extensively. Generally, for application in the present invention, a pulp with a CSF of below 100 is used, and preferably, the CSF should be less than or equal to about 45.

The pulp is treated with a cationic material in such a manner as to allow the cationic material to coat at least a portion of the surface of at least some of the fibers thereby imparting a charge on the fibers. Methods of applying the cationic material to the fibers are known in the art and include, but are not limited to, spray, dip, or submergence coating to cause adsorption, chemical reaction or crosslinking of the cationic material to the surface of the fibers. The treated pulp is then rinsed in reverse osmosis/deionized (RO/DI) water, partially dewatered, usually under vacuum, to produce a precoat that can then be exposed to a biologically active metal salt solution. The use of nearly ion-free rinse water causes the counter-ions associated with the cationic material to be drawn tightly against the treated fiber surface and to eliminate unwanted ions that may cause uncontrolled precipitation of the biologically active metal into sites remote from the cationic surface.

The metal salt solution is infiltrated into the fibers to allow precipitation of the cationic metal colloid complex on a surface of at least a portion of the fibers. The precipitation accurately deposits a metal colloid adjacent to the cationic coating because the counter-ion associated with this coating reacts with the applied metal salt to form colloidal particles. After sufficient exposure to the biologically active metal salt solution, the fibers can be rinsed and excess water is removed. When silver nitrate is used as the metal salt solution, the presence of precipitated silver can be confirmed by using a Kratos EDX-700/800 X-ray fluorescence spectrometer available from Kratos Analytical, a Shimadzu Group Company, Japan.

One or more additives either in a particulate, fiber, whisker, or powder form may also be mixed with the microbiological interception enhanced filter aid to adsorb other contaminants or participate in the interception of microbiological or other contaminants. Useful additives may include, but are not limited to, metallic particles, activated alumina, activated carbon, silica, polymeric powders and fibers, glass beads or fibers, cellulose fibers, ion-exchange resins, engineered resins, ceramics, zeolites, diatomaceous earth, activated bauxite, fuller's earth, calcium sulfate, other adsorbent materials such as super adsorbent polymers (SAPs), or combinations thereof. The additives can also be chemically treated to impart microbiological interception capabilities depending upon the particular application. Such additives are preferably present in a sufficient amount such that the fluid flow in the resultant precoat composition and/or filter cake is not substantially impeded when used in filtration applications. The amount of additives is dependent upon the particular use of the filtration system.

The microbiological interception enhanced filter aid can be mixed with bulk filter aids in a minority amount from about 0.5% to about 50% by weight of a precoat composition to enhance the performance of the bulk filter aid.

Method of Using the Microbiological Interception Enhanced Filter Aid in a Precoat Composition of the Present Invention A dispersion that includes the microbiological interception enhanced filter aid in a fluid is passed through a support medium, such as a septum or filter screen, and a precoat having a thickness of, generally, about 0.5 to about 3 millimeters is formed on the support medium. The support medium is of a size and square footage that the flow rate of the fluid to be filtered is not so slow as to be prohibitive in a large scale manufacturing process. The fluid to be filtered is passed through the filter cake and the particulate and microbiological contaminants are captured on the filter cake. A body feed composition that can include the microbiological interception enhanced filter aid may be mixed with the fluid prior to filtration through the filter cake. The addition of the body feed composition opens up the permeability of the filter cake and prevents the formation of an impervious web of captured contaminants on the filter cake. When filtration is terminated, the filter cake is back flushed and the filter cake falls off the support medium. The spent filter cake is disposed of as a cake or slurry.

A precoat composition comprising the microbiological interception enhanced filter aid can provide at least about 3 log reduction in microbiological contaminants, including viruses, thereby providing a single-step cold sterilization technique. If such comprehensive interception is unnecessary, the microbiological interception enhanced filter aid can be mixed with an uncharged bulk filter aid in an amount of about 0.5% to about 50% by weight of the precoat composition to provide the desired level of interception.

Examples

The following examples are provided to illustrate the present invention and should not be construed as limiting the scope of the invention.

Bacterial challenges of the filter aids were performed using suspensions of *Escherichia coli* of the American Type Culture Collection (ATCC) No. 11775 to evaluate the response to a bacterial challenge. The Standard Operating Procedures of the ATCC were used for propagation of the bacterium, and standard microbiological procedures, as well known in the art, were used for preparing and quantifying the bacteria in both the influent and effluent of filter aids challenged with the bacterial suspensions.

The precoated surfaces used in the following examples had a diameter of 47 millimeters and were formed on an Osmonics/MSI GRAVI-SEAL™ Analytical Funnel available from Fischer Sceintific, Pittsburgh, Pa. The analytical funnel was lined with a spun-bonded polyester commercially available from BBA Nonwovens Reemay, Inc., of Old Hickory, Tenn., under the trade name REEMAY™ 2004.

Example 1 (Comparative)

Interception of *E. coli* by Untreated Cellulose

Alpha-Cel BH-40 cellulose pulp, available from International Fiber Corporation, having a dry weight of about 0.63 g, was formed into a precoat in the analytical funnel. RO/DI water was passed through the precoat using a peristaltic pump to achieve a flow rate of 31 ml/minute. The precoat was challenged with a bacterial suspension containing $1.06 \times 10^5$ *E. coli*. The log reduction value of the precoat containing untreated cellulose pulp was less than about 1.

Example 2 (Comparative)

Interception of *E. coli* on Untreated Cellulose Admixed with 5% of Untreated Lyocell Nanofibers A precoat was made using 0.60 g dry weight of BH-40 cellulose pulp admixed with 0.03 g dry weight of untreated fibrillated lyocell fibers in 350 ml of RO/DI water. RO/DI water was passed through the precoat at a flow rate of about 80 ml/minute using a peristaltic pump. The precoat was challenged with a bacterial suspension containing $1.06 \times 10^5$ *E. coli*. The log reduction value of the precoat was less than about 1.

Example 3 (Comparative)

Interception of *E. coli* by Untreated Cellulose Admixed with 5% of a Filter Aid Made with Lyocell Fibers Treated with a Cationic Material Fibrillated lyocell nanofibers having a Canadian Standard Freeness of 45 in an amount of about 11.4 g dry weight (120.0 g wet weight) were dispersed in 1.0 L of RO/DI water with 3.0 ml of MERQUAT® 100 as a 30% aqueous solution and 0.27 g of sodium bromide overnight. The resultant charged fibers were poured into a standard 8 inch Brit filter fitted with a 100 mesh forming wire and excess water removed under vacuum forming a pulp sheet. The pulp sheet was rinsed with 500 ml of RO/DI water.

A precoat was made using 0.60 g dry weight of BH-40 cellulose pulp admixed with 0.03 g dry weight of the charged, fibrillated lyocell fibers. RO/DI water was passed through the precoat at a flow rate of about 28 ml/minute using a peristaltic pump. The precoat was challenged with a bacterial suspension containing $1.06 \times 10^5$ *E. coli*. The log reduction value of the precoat was about 2.10.

Example 4

Interception of *E. coli* by Untreated Cellulose Admixed with 5% of the Microbiological Interception Enhanced Filter Aid Fibrillated lyocell nanofibers having a Canadian Standard Freeness of 45 in an amount of about 11.4 g dry weight (120.0 g wet weight) were dispersed in 1.0 L of RO/DI water with 3.0 ml of MERQUAT® 100 as a 30% aqueous solution and 0.27 g of sodium bromide overnight. The resultant charged fibers were poured into a standard 8 inch Brit jar fitted with a 100 mesh forming wire and excess water removed under vacuum forming a pulp sheet. The pulp sheet was rinsed with 500 ml of RO/DI water. A dilute silver nitrate solution, 3.0 ml of a stock solution (1.8 g AgNO3 in 60 ml RO/DI water) was diluted by adding 60 ml RO/DI water, and poured uniformly over the pulp sheet to provide full exposure and saturation. The silver nitrate solution was left on the pulp sheet for at least about 15 minutes and excess water removed under vacuum pressure to yield the microbiological interception enhanced filter aid of the present invention.

A precoat was made using 0.60 g dry weight of untreated BH-40 cellulose pulp admixed with 0.03 g dry weight of the microbiological interception enhanced filter aid. RO/DI water was passed through the precoat at a flow rate of about 31 ml/minute using a peristaltic pump. The precoat was challenged with a bacterial suspension containing $1.06 \times 10^5$ *E. coli*. The log reduction value of the precoat was about 5.02, indicating complete removal of the *E. coli*.

Example 5

Interception of *E. coli* by the Microbiological Interception Enhanced Filter Aid RO/DI water was passed through a precoat of 0.63 g dry weight of the microbiological interception enhanced filter aid as described in Example 4 at a flow rate of about 28 ml/minute using a peristaltic pump. The precoat was challenged with a bacterial suspension containing $1.0 \times 10^4$ *E. coli*. The log reduction value of the microbiological interception enhanced filter aid was 4.00, indicating complete removal of the *E. coli*.

The results of Examples 1 through 5 are shown in Table 1 below.

TABLE I

Log Reduction Values Of *E. coli* For Examples 1 Through 5

| Ex # | % by wt. MIEFA | *E. coli* challenge | # CFU | LRV |
| --- | --- | --- | --- | --- |
| 1 | 0 | $1.06 \times 10^5$ | $2.00 \times 10^4$ | <1 |
| 2 | 0 | $1.06 \times 10^5$ | $3.20 \times 10^4$ | <1 |
| 3 | 0 | $1.06 \times 10^5$ | $8.33 \times 10^2$ | 2.10 |
| 4 | 5% | $1.06 \times 10^5$ | 0 | 5.02 |
| 5 | 100% | $1.0 \times 10^4$ | 0 | 4.00 |

MIEFA = Microbiological Interception Enhanced Filter Aid of the present invention.
CFU = Colonies forming units per plate.

The addition of even a small quantity of the microbiological interception enhanced filter aid of the present invention appears to provide significant microbiological interception capability to a precoat composition for reduction of *E*.

coli as shown in Example 4. The precoat composition of Example 5 comprising only the microbiological interception enhanced filter aid provided excellent bacterial interception.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

What is claimed is:

1. A composition comprising:
   a filter aid having coated on at least a portion thereof, a cationic material having a counter ion associated therewith, wherein a biologically active metal is precipitated with the counter ion in direct proximity to the cationic material.

2. The composition of claim 1 wherein said filter aid is used to form a filter cake on a septum prior to filtration.

3. The composition of claim 1 wherein said filter aid can be combined with an influent as a body feed composition.

4. The composition of claim 1 wherein said filter aid comprises nanofibers, cellulose, diatomaceous earth, activated carbon, activated alumina, silicates, polymeric resins or fibers, or combinations thereof.

5. The composition of claim 1 wherein said filter aid is admixed with an untreated filter aid material.

6. The composition of claim 1 wherein the cationic material is selected from the group consisting of quaternized amines, quaternized amides, quaternary ammonium salts, quaternized imides, benzalkonium compounds, cationic aminosilicon compounds, polymers thereof, and combinations thereof.

7. The composition of claim 1 wherein the cationic material has a medium to high charge density and a molecular weight greater than about 5000 Daltons.

8. The composition of claim 1 wherein the cationic material is a homopolymer of diallyl dimethyl ammonium halide.

9. The composition of claim 1 wherein the biologically active metal is silver, copper, zinc, cadmium, mercury, antimony, gold, aluminum, platinum, palladium, or combinations thereof.

10. The composition of claim 1 wherein said filter aid comprises fibers having a Canadian Standard Freeness of less than or equal to about 45.

11. A composition comprising:
    an adsorbent;
    a filter aid admixed with said adsorbent, said filter aid having coated on at least a portion thereof, a cationic material having a counter ion associated therewith and a biologically active metal precipitated with the counter ion in direct proximity to the cationic material.

12. The composition of claim 11 wherein said adsorbent comprises cellulose fibers and wherein said filter aid comprises fibrillated lyocell fibers having a Canadian Standard Freeness of less than or equal to about 100.

13. A method of filtering an influent:
    providing a support medium;
    coating the support medium with a filter aid to form a precoat, the filter aid having coated on at least a portion thereof, a cationic material having a counter ion associated therewith and a biologically active metal precipitated with the counter ion in direct proximity to the cationic material;
    passing the influent through the precoat;
    retaining contaminants from the influent on the precoat; and
    obtaining a clarified effluent.

14. The method of claim 13 further including the step of adding the filter aid to the influent prior to the step of passing the influent through the precoat.

15. The method of claim 13 wherein in the step of coating the support medium with the filter aid, the filter aid comprises nanofibers, cellulose, diatomaceous earth, activated carbon, activated alumina, silicates, polymeric resins or fibers, or combinations thereof.

16. The method of claim 13 wherein in the step of coating the support medium with the filter aid, the filter aid is admixed with an untreated filter aid material.

17. The method of claim 13 wherein in the step of coating the support medium with the filter aid, the filter aid is coated with a cationic material selected from the group consisting of quaternized amines, quaternized amides, quaternary ammonium salts, quaternized imides, benzalkonium compounds, cationic aminosilicon compounds, polymers thereof, and combinations thereof.

18. The method of claim 13 wherein in the step of coating the support medium with the filter aid, the filter aid is coated with a homopolymer of diallyl dimethyl ammonium halide.

19. The method of claim 13 wherein in the step of coating the support medium with the filter aid, the biologically active metal is silver, copper, zinc, cadmium, mercury, antimony, gold, aluminum, platinum, palladium, or combinations thereof.

20. The method of claim 13 further including the step of providing at least about 4 log reduction of microbiological contaminants in the influent.

* * * * *

UNITED STATES PATENT AND TRADEMARK OFFICE
CERTIFICATE OF CORRECTION

PATENT NO.    : 6,660,172 B2
DATED         : December 9, 2003
INVENTOR(S)   : Koslow, Evan E.

It is certified that error appears in the above-identified patent and that said Letters Patent is hereby corrected as shown below:

<u>Column 1,</u>
Line 7, "January 31, 2001" should be -- January 31, 2002 --.

Signed and Sealed this

Twenty-fifth Day of May, 2004

JON W. DUDAS
*Acting Director of the United States Patent and Trademark Office*